(12) United States Patent
Gorres

(10) Patent No.: US 8,343,122 B2
(45) Date of Patent: *Jan. 1, 2013

(54) DEVICE FOR MONITORING A PATIENT FOR A URINARY TRACT INFECTION

(76) Inventor: Geoffrey H Gorres, Amery, WI (US)

( * ) Notice: Subject to any disclaimer, the term of this patent is extended or adjusted under 35 U.S.C. 154(b) by 301 days.

This patent is subject to a terminal disclaimer.

(21) Appl. No.: 12/766,417

(22) Filed: Apr. 23, 2010

(65) Prior Publication Data

US 2010/0274156 A1 Oct. 28, 2010

Related U.S. Application Data

(63) Continuation of application No. 11/318,769, filed on Dec. 27, 2005, now Pat. No. 7,727,206.

(51) Int. Cl.
*A61F 5/44* (2006.01)
*A61M 27/00* (2006.01)
*A61M 31/00* (2006.01)
*A61M 37/00* (2006.01)
*A61M 1/00* (2006.01)
*G01N 21/00* (2006.01)
*G01N 21/75* (2006.01)
*G01N 33/53* (2006.01)
*B01L 3/00* (2006.01)
*C12Q 1/00* (2006.01)
*C12Q 1/58* (2006.01)

(52) U.S. Cl. .......... 604/349; 604/48; 604/500; 604/82; 604/93.01; 604/318; 604/327; 604/408; 604/544; 422/55; 422/56; 422/57; 422/58; 422/61; 422/68.1; 436/164; 436/810; 435/4; 435/7.1; 435/7.4; 435/7.9; 435/12; 435/286.2; 435/287.1; 435/810; 435/975

(58) Field of Classification Search .......... 604/349, 604/48, 500, 82, 93.01, 318, 327, 408, 544; 422/55, 56, 57, 58, 61, 68.1; 436/164, 810; 435/4, 7.1, 7.4, 7.9, 12, 286.2, 287.1, 810, 435/975

See application file for complete search history.

(56) References Cited

U.S. PATENT DOCUMENTS

| | | |
|---|---|---|
| 3,359,072 A | 12/1967 | Rey et al. |
| 3,418,079 A | 12/1968 | Rey et al. |
| 3,438,737 A | 4/1969 | Atkinson et al. |
| 3,722,502 A | 3/1973 | Besuner et al. |
| 3,817,239 A | 6/1974 | Kuntz |

(Continued)

FOREIGN PATENT DOCUMENTS

WO    WO 01/33215    5/2001

(Continued)

OTHER PUBLICATIONS

Online encyclopedia article, "sodium nitrite." Accessed Apr. 1, 2008. http://en.wikipedia.org/wiki/Sodium.sub.--nitrite.

(Continued)

*Primary Examiner* — Leslie Deak
*Assistant Examiner* — Adam Marcetich
(74) *Attorney, Agent, or Firm* — Fish & Richardson P.C.

(57) ABSTRACT

The invention provides for a urinary monitoring device to monitor for the presence or absence of markers indicative of a urinary tract infection (UTI). The invention also provides for methods of using such a device.

19 Claims, 4 Drawing Sheets

U.S. PATENT DOCUMENTS

| | | | |
|---|---|---|---|
| 4,013,416 A | | 3/1977 | Rittersdorf et al. |
| 4,076,502 A | | 2/1978 | Dugle et al. |
| 4,206,767 A | | 6/1980 | Wingrove |
| 4,225,410 A | * | 9/1980 | Pace ............................ 204/412 |
| 4,278,763 A | | 7/1981 | Berger et al. |
| 4,303,753 A | | 12/1981 | Lam |
| 4,331,760 A | | 5/1982 | Berger et al. |
| 4,434,235 A | | 2/1984 | Rabi et al. |
| 4,452,682 A | * | 6/1984 | Takata et al. ............. 204/403.12 |
| 4,469,789 A | | 9/1984 | Berger et al. |
| 4,535,786 A | | 8/1985 | Kater |
| 4,551,428 A | | 11/1985 | Berger et al. |
| 4,575,371 A | | 3/1986 | Nordqvist et al. |
| 4,579,554 A | | 4/1986 | Glassman |
| 4,637,979 A | | 1/1987 | Skjold et al. |
| 4,645,842 A | | 2/1987 | Corey et al. |
| 4,657,855 A | | 4/1987 | Corey et al. |
| 4,704,460 A | | 11/1987 | Corey |
| 4,753,249 A | | 6/1988 | Muller |
| 4,758,508 A | | 7/1988 | Schnabel et al. |
| 4,786,394 A | * | 11/1988 | Enzer et al. ................... 204/401 |
| 4,806,313 A | | 2/1989 | Ebersole et al. |
| 4,813,935 A | | 3/1989 | Haber et al. |
| 4,846,005 A | | 7/1989 | Bacehowski et al. |
| 4,865,046 A | | 9/1989 | Duran |
| 4,936,837 A | | 6/1990 | Wexler et al. |
| 4,976,270 A | | 12/1990 | Parl et al. |
| 5,071,769 A | | 12/1991 | Kundu et al. |
| 5,141,850 A | | 8/1992 | Cole et al. |
| 5,165,406 A | | 11/1992 | Wong |
| 5,194,133 A | * | 3/1993 | Clark et al. ................... 204/608 |
| 5,295,979 A | | 3/1994 | DeLaurentis et al. |
| 5,300,051 A | | 4/1994 | Lageson |
| 5,312,379 A | | 5/1994 | Rahe |
| 5,320,969 A | | 6/1994 | Bauer et al. |
| 5,330,634 A | | 7/1994 | Wong et al. |
| 5,403,744 A | | 4/1995 | Zimmerle |
| 5,405,510 A | * | 4/1995 | Betts et al. .................... 205/782 |
| 5,476,434 A | | 12/1995 | Kalb et al. |
| 5,505,828 A | | 4/1996 | Wong et al. |
| 5,512,450 A | | 4/1996 | Johnson et al. |
| 5,602,040 A | | 2/1997 | May et al. |
| 5,605,161 A | | 2/1997 | Cross |
| 5,622,871 A | | 4/1997 | May et al. |
| 5,656,503 A | | 8/1997 | May et al. |
| 5,663,044 A | | 9/1997 | Noffsinger et al. |
| 5,704,353 A | | 1/1998 | Kalb et al. |
| 5,712,172 A | | 1/1998 | Huang et al. |
| 5,750,359 A | | 5/1998 | Huh et al. |
| 5,758,643 A | | 6/1998 | Wong et al. |
| 5,759,860 A | | 6/1998 | Smith et al. |
| 5,776,715 A | | 7/1998 | Garnham |
| 5,776,780 A | | 7/1998 | Smith et al. |
| 5,785,694 A | | 7/1998 | Cohen et al. |
| 5,858,697 A | | 1/1999 | Groner et al. |
| 5,897,993 A | * | 4/1999 | Sato et al. ........................ 435/29 |
| 5,902,253 A | | 5/1999 | Pfeiffer et al. |
| 5,919,170 A | | 7/1999 | Woessner |
| 5,944,660 A | | 8/1999 | Kimball et al. |
| 5,976,085 A | | 11/1999 | Kimball et al. |
| 6,013,465 A | | 1/2000 | Schmitz-Treyer et al. |
| 6,096,275 A | | 8/2000 | Greenberg |
| 6,117,120 A | | 9/2000 | Heininger |
| 6,162,201 A | | 12/2000 | Cohen et al. |
| 6,277,646 B1 | | 8/2001 | Guirguis et al. |
| 6,372,182 B1 | | 4/2002 | Mauro et al. |
| 6,375,627 B1 | | 4/2002 | Mauze et al. |
| 6,375,897 B1 | | 4/2002 | Bachand |
| 6,444,169 B1 | | 9/2002 | Evtodienko et al. |
| 6,495,823 B1 | | 12/2002 | Miller et al. |
| 6,572,564 B2 | | 6/2003 | Ito et al. |
| 6,617,156 B1 | | 9/2003 | Doucette-Stamm et al. |
| 6,690,004 B2 | | 2/2004 | Miller et al. |
| 6,806,463 B2 | | 10/2004 | Miller et al. |
| 6,833,111 B2 | * | 12/2004 | Robertson et al. ............ 422/430 |
| 6,837,868 B1 | | 1/2005 | Fajnsztajn |
| 6,855,491 B2 | | 2/2005 | Small et al. |
| 7,338,480 B2 | | 3/2008 | Nakajima et al. |
| 7,651,468 B2 | | 1/2010 | Mulder |
| 7,931,630 B2 | * | 4/2011 | Nishtala et al. ............... 604/318 |
| 2002/0103460 A1 | | 8/2002 | Kubalak et al. |
| 2004/0191919 A1 | | 9/2004 | Unger et al. |
| 2005/0051719 A1 | | 3/2005 | Miller et al. |
| 2005/0240164 A1 | * | 10/2005 | Perlhagen et al. ............ 604/347 |
| 2005/0245840 A1 | | 11/2005 | Christopher et al. |
| 2005/0256447 A1 | * | 11/2005 | Richardson et al. ............ 604/65 |
| 2006/0271019 A1 | | 11/2006 | Stoller et al. |
| 2007/0010797 A1 | | 1/2007 | Nishtala et al. |
| 2007/0092402 A1 | | 4/2007 | Wu et al. |

FOREIGN PATENT DOCUMENTS

| WO | WO 02/079749 | 10/2002 |
|---|---|---|

OTHER PUBLICATIONS

"Guideline for Prevention of Catheter-associated Urinary Tract Infections," [online]. CDC Issues in Healthcare Settings, 1981, [retrieved on Dec. 2, 2005 from the Internet: <URL: www.cdc.gov/ncidod/hip/guide/uritract.htm>, 9 pages].

Angus et al., "Epidemiology of severe sepsis in the United States: Analysis of incidence, outcome, and associated costs of care," *Crit. Care Med.*, 2001, 29(7):1303-1310.

Bartlett et al., "Screening for Urinary Tract Infection With the Yellow IRIS" *Lab. Med.*, 1992, 23(9):599-602.

Beer et al., "False positive results for leucocytes in urine dipstick test with common antibiotics," *Brit. Med. J.*, 1996, 313:25.

Begany, "The National Impact of Severe Sepsis" [online]. Pulmonary Reviews.Com, 2001, [retrieved on Dec. 2, 2005 from the Internet: <URL: www.pulmonaryreview.com/oct01/pr.sub.--oct01.sub.--sepsis.html>, 4 pages].

Czerwinski et al., "Further evaluation of the Griess test to detect significant bacteriuria. Part II," *Am. J. Obstet. Gynecol.*, 1971, 110(5):677-681.

Fuchs and Gutensohn, *Dtsch. Med. J.*, 1967, 10:342-347 (w/ English summary).

Griebling, "Urinary Tract Infection in Men," Urologic Diseases in America Interim Compendium, 2004, Ch. 7, U.S. Government Publishing Office, pp. 187-209.

Griebling, "Urinary Tract Infection in Women," Urologic Diseases in America Interim Compendium, 2004, Ch. 6, U.S. Government Publishing Office, pp. 154-180.

Maki and Tambyah, "Engineering Out the Risk of Infection with Urinary Catheters," *Emerging Infectious Diseases*, 2001, 7(2):1-6.

Murphy, "Deaths: Final Data for 1998. National Vital Statistics Reports," at www.cdc.gov/nchs/dtat/mvs48.sub.--11.pdf, 2000, 48(11):1-106.

Notelovitz et al., "Evaluation of a Rapid Bedside Screening Test for Asymptomatic Urinary Tract Infection—A Preliminary Communication," *S. A. Med. J.*, 1970, 44:1128-1131.

Rhinehart, "Infection Control in Home Care" [online]. CDC Emerging Infectious Diseases, [retrieved on Dec. 2, 2005 from the Internet: <URL: www.cdc.gov/ncidod/Eid/v17no2/rhinehart.htm>, 9 pages].

Sands, et al., "Epidemiology of Sepsis Syndrome in 8 Academic Medical Centers," *JAMA*, 1997, 278(3):234-240.

Simerville et al., "Urinalysis: A Comprehensive Review," *Am. Fam. Physician*, 2005, 71(6):1153-1162.

Vaitukaitis et al., "A radioimmuoassay which specifically measures human chorionic gonadotropin in the presence of human luteizining hormone," *Am. J. Obstet. Gynecol.*, 1972, 113(6):751-758.

Young and Soper, "Urinalysis and urinary tract infection: update for clinicians," *Infect. Dis. Obstet. Gynecol.*, 2001, 9:249-255.

Kuntz, "Bedside Diagnosis of Urinary Infection," *West J Med*, 1978, 129:94-96.

* cited by examiner

STANDING ORDERS FOR UTI-MONITORING DEVICE

Date:
Time:

ALLERGIES:

Foley catheter to gravity drainage; use system with URINARY MONITORING DEVICE

Check URINARY MONITORING DEVICE with scheduled Vital Signs, and record "POS" (+/positive), or "NEG" (-/negative) on flowsheet If device indicator is POSITIVE, do the following:

-Send urine sample to lab for UA with microscopic exam, and Urine Culture and Sensitivity; inform lab of any current antibiotic therapy, and if antibiotic therapy chosen below -Start patient on:  _____ NO ANTIBIOTICS, await lab results
OR
_____ Ciprofloxacin, 400 mg IV q 12 hours
OR
_____ Ciprofloxacin, 500 mg PO bid
OR
_____ _____

-Give first dose of selected antibiotic NOW

-Notify attending physician of positive result    _____ Now
_____ On Rounds

Signed:_____

FIGURE 4

DEVICE FOR MONITORING A PATIENT FOR A URINARY TRACT INFECTION

CROSS-REFERENCE TO RELATED APPLICATIONS

This application is a Continuation application and claims the benefit of priority under 35 U.S.C. §120 to U.S. application Ser. No. 11/318,769 filed Dec. 27, 2005.

TECHNICAL FIELD

This invention relates to medical devices, and more particularly to a device for monitoring a patient for a urinary tract infection.

BACKGROUND

Urinary tract infections are a major cause of morbidity and mortality in healthcare, especially in hospitalized and otherwise debilitated patients. Catheter-associated UTI (CAUTI) is the most common nosocomial infection, accounting for more than 40% of all hospital-acquired infection. The risk of infection is substantially increased in patients having a urinary catheter. In addition, many afflicted patients are unable to verbalize their symptoms and their infections may not be recognized until they are in advanced stages such as life-threatening sepsis.

CAUTI is the second most common cause of nosocomial sepsis after pneumonia. More than 750,000 patients in the United States develop severe sepsis each year, which is characterized by acute organ system dysfunction. The mortality rate from severe sepsis, at 28.6%, leaves 215,000 Americans dead annually at an estimated cost of about $16.7 billion. This is nearly 600 patients per day, which means that as many patients in the United States die from severe sepsis each day as die from acute myocardial infarction.

Obviously, it is desirable to discover catheter-associated UTI's as early as possible. Urine "dipsticks" are available (e.g., Multistix®, Bayer, Leverkusen, Germany; Chemistrip®, Roche Diagnostics, Indianapolis, Ind.; Multistix® 10 SG, Miles Laboratories, Inc., Elkhart, Ind.; and Combur-Test®, Boehringer Mannheim Corp., Indianapolis, Ind.), but require an index of suspicion, are labor-intensive for nursing staff, and usually require incident-specific physician orders. More commonly, urine specimens are sent to a hospital or central laboratory when certain indicators such as cloudiness, a change in color, and/or blood are observed.

Current procedures can result in a significant lapse of time before the UTI is clinically diagnosed and treatment initiated. Ultimately, the cost of these infections in both dollars and human life is substantial. The present disclosure provides systems and devices that monitor a patient for a UTI as well as methods of using such systems and devices. Using the disclosed systems and devices, particularly on catheterized patients, can significantly reduce or completely eliminate the current delays in diagnosis and treatment of UTIs.

SUMMARY

In one aspect, the invention provides a urinary tract infection (UTI)-monitoring urinary catheter system for monitoring the presence or absence of one or more markers in urine that are indicative of a urinary tract infection (UTI). Such a UTI-monitoring system generally includes a catheter portion, a collection tubing portion, and a collection bag portion. At least one of those portions includes a UTI indicator substrate that detects and signals the presence or absence of the one or more markers in urine that are indicative of a UTI. In certain embodiments, the catheter portion contains the UTI indicator substrate; in certain embodiments, the collection tubing portion contains the UTI indicator substrate; and in certain embodiments, the collection bag portion contains the UTI indicator substrate.

In another aspect, the invention provides a UTI monitoring device for monitoring the presence or absence of one or more markers in urine that are indicative of a urinary tract infection (UTI). Such a UTI-monitoring device can be configured for placement in-line in a urinary catheter system. Such a UTI-monitoring device generally includes a tubular portion that has a first port on one end and a second port on the other end that are configured for in-line placement at a position along a urinary catheter system. The tubular portion of such a device also includes a UTI indicator substrate for detecting and signaling the presence or absence of the one or more markers in urine that are indicative of a UTI.

The UTI indicator substrate can be attached (e.g., releasably attached) to an inside surface of the at least one portion of the UTI-monitoring system or device. In some embodiments, a UTI-monitoring system or device contains more than one UTI indicator substrate. Representative markers in urine that are indicative of a UTI include leukocyte esterase and/or nitrites. A UTI indicator substrate can include at least one detector component and at least one signal component. Representative detector components include an antibody that has specific binding affinity for the one or more markers in urine that are indicative of a UTI, and representative signal components include a colorimetric change and a digital readout.

In still another aspect, the invention provides methods of monitoring a catheterized patient's urine for the presence or absence of one or more markers indicative of a UTI. Such a method comprises catheterizing the patient with the UTI-monitoring urinary catheter system as described herein or placing a UTI-monitoring device as described herein in a urinary catheter system, and monitoring the patient's urine for the presence or absence of one or more markers indicative of a UTI.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

FIG. 4 is a representative example of standing orders that a physician can use when a UTI-monitoring system or device is employed.

Like reference symbols in the various drawings indicate like elements.

DETAILED DESCRIPTION

Urinary tract infection (UTI)-monitoring systems and devices are disclosed herein. The systems and devices disclosed herein provide timely, sensitive, and specific information regarding the presence or absence of markers in urine that are indicative of a UTI. The systems and devices disclosed herein provide timely information regarding UTIs, which is specifically valuable in patients who have a urinary catheter system in place. Urinary catheter systems are well known in the art, and generally include a catheter portion, a collection tubing portion, and a collection bag portion. See, for example, U.S. Pat. Nos. 4,575,371; 4,579,554; 4,813,935; 4,936,837; 5,295,979; 5,300,051; 5,785,694; 5,919,170; 6,117,120; 6,162,201; and 6,837,868.

This disclosure describes a UTI-monitoring urinary catheter system, which is useful for monitoring the presence or absence of one or more markers in urine that are indicative of a urinary tract infection (UTI). A UTI-monitoring urinary catheter system typically includes a catheter portion, a collection tubing portion, and a collection bag portion. At least one of those portions, in a UTI-monitoring urinary catheter system, contains a UTI indicator substrate. A UTI indicator substrate detects and signals to a user whether or not one or more markers are present in the urine that are indicative of a UTI.

Figure 1:
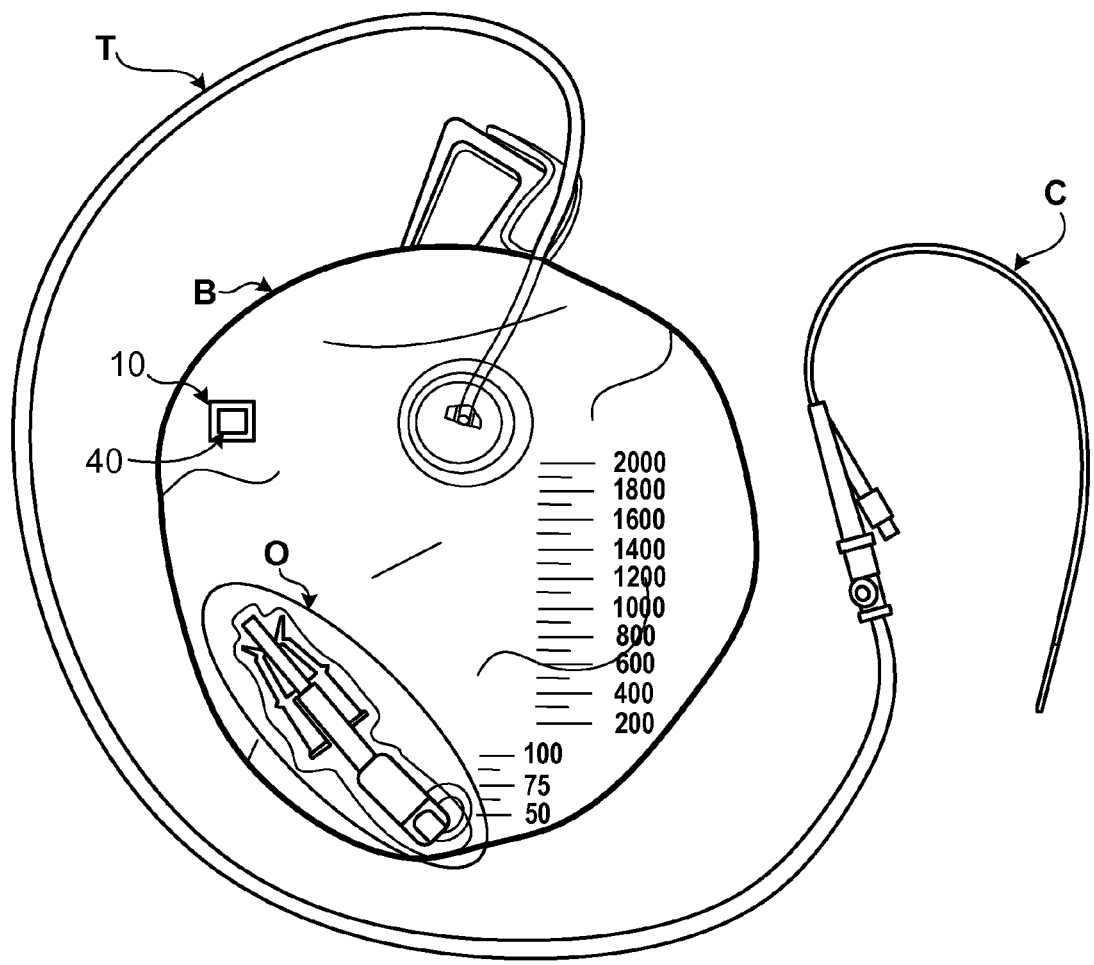
FIG. 1 is a schematic of one embodiment of a UTI-monitoring urinary catheter system in which the UTI indicator substrate is attached to the inside wall of the collection bag portion.

FIG. 1 shows one representative example of a UTI-monitoring urinary catheter system. The UTI-monitoring urinary catheter system shown in FIG. 1 includes a conventional Foley catheter system having a urinary catheter C portion, a collection tubing T portion, and a collection bag B portion. A drainage outlet O also is shown on collection bag B. In the embodiment shown in FIG. 1, a UTI indicator substrate 40 is attached to the inside surface of the collection bag B. A UTI indicator substrate 40 can be attached to the inside surface of any portion of a urinary catheter system, however, provided that the UTI indicator substrate 40 comes into contact, at least momentarily, with the urine moving through the urinary catheter system. One or more UTI indicator substrates can be placed within one or more portions of the urinary catheter system during, for example, the manufacturing process.

In some embodiments, one or more portions of a urinary catheter system (e.g., the catheter portion, the collection tubing portion, or the collection bag portion) can contain a receptacle or the like into which a UTI indicator substrate can be placed. It is envisioned that receptacles or the like can be designed in a urinary catheter system that allow for removing one (e.g., used) indicator substrate and replacing it with another (e.g., fresh) indicator substrate. Such a receptacle or the like must allow for the UTI indicator substrate to contact the urine, however, it is understood by those in the art that the use of any type of releasable, removable, or replaceable UTI indicator substrate must not jeopardize the sterility and integrity of the closed urinary catheter system.

This disclosure also describes a UTI-monitoring device. Similarly to a UTI-monitoring urinary catheter system, a UTI-monitoring device is useful for monitoring the presence or absence of one or more markers in urine that are indicative of a UTI. A UTI-monitoring device can be a device that is configured, for example, for in-line placement in a conventional urinary catheter system. For example, a UTI-monitoring device can be configured to be placed in-line within a catheter portion, a collection tubing portion, or a collection bag portion, or as an in-line fitting for placement between a catheter portion and a collection tubing portion or between a collection tubing portion and a collection bag portion. As with the removal or replacement of a UTI indicator substrate in a UTI-monitoring urinary catheter system, the placement or replacement of a UTI-monitoring device (e.g., in-line) by a user must not jeopardize the sterility and integrity of the closed system.

Figure 2:
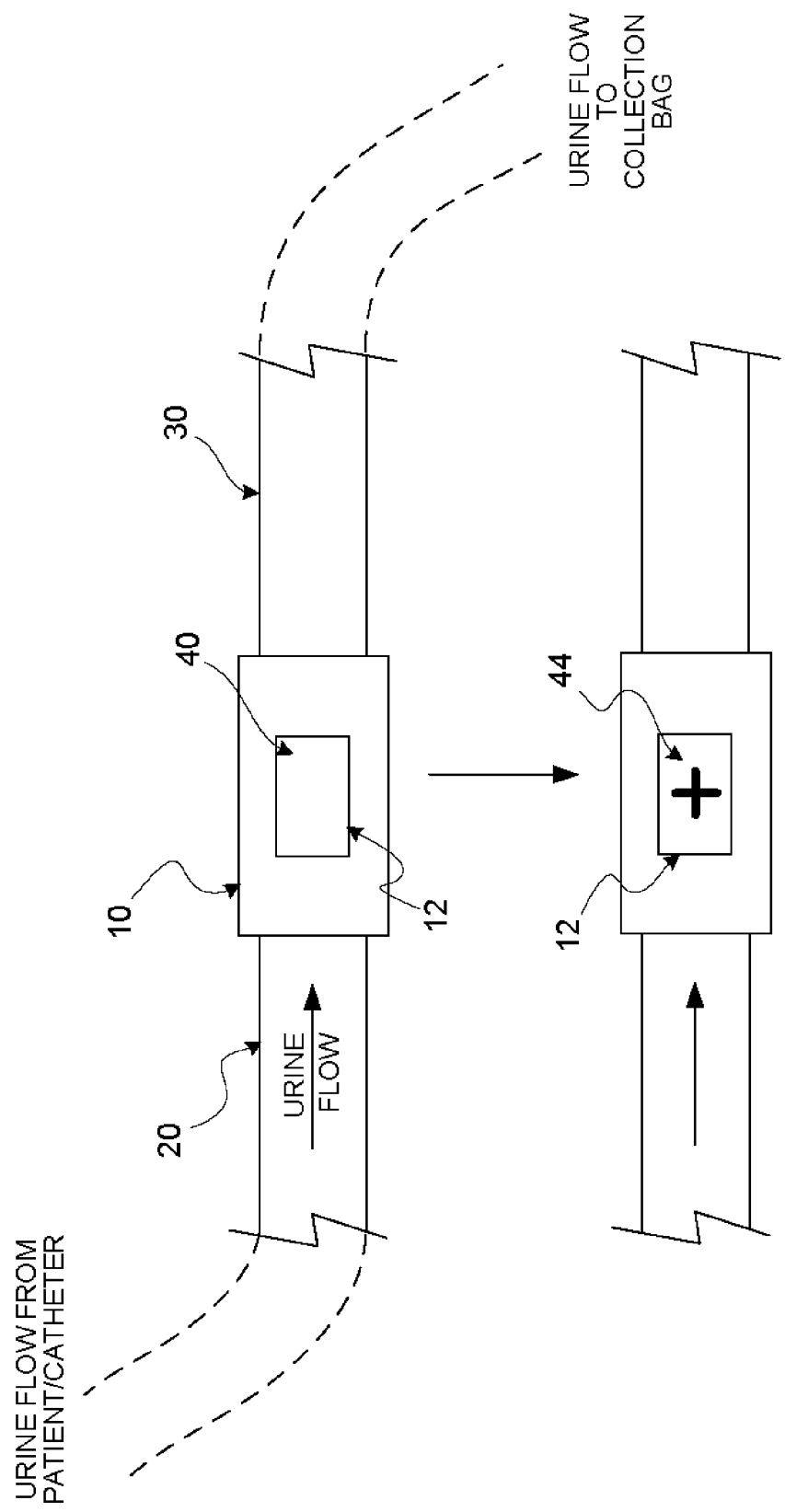
FIG. 2 is a schematic showing one embodiment of a UTI-monitoring device that can be positioned in-line in a urinary catheter system.

FIG. 2 shows a UTI-monitoring device for in-line placement. An in-line UTI-monitoring device generally has a tubular portion 10 through which urine flows. The UTI-monitoring device shown in FIG. 2 has a UTI indicator substrate 40 attached to the inside wall of the tubular portion 10 positioned in such a way that the UTI substrate indicator 40 comes into contact with the urine. The tubular portion 10 of an in-line UTI-monitoring device generally has an appropriately sized first port 20 on one end and an appropriately sized second port 30 on the other end for in-line placement in a urinary catheter system. In the embodiment shown in FIG. 2, the signal 44 is visible through a window 12 in the tubular chamber 10. The signal in FIG. 2 is shown as a 'plus' sign, which indicates, for example, a positive result (i.e., the presence of a UTI marker in the urine).

A UTI-monitoring device can be manufactured in individual units that are placed in-line in a urinary catheter system by a user (e.g., a nurse, attendant, or caretaker). Alternatively, a UTI-monitoring device can be manufactured as an integral part of one or more of the portions of a urinary catheter system. A UTI-monitoring device also can have features such as an anti-reflux valve to minimize or eliminate any backflow of urine. Although a UTI-monitoring device is disclosed herein that is configured for in-line placement, a UTI-monitoring device can have any number of configurations provided that the UTI indicator substrate or a component thereof contacts the urine traveling through or collected in a urinary catheter system.

As an alternative to a UTI indicator substrate being attached to the inside wall of a portion of a UTI-monitoring system or a UTI-monitoring device, a UTI indicator substrate 40 can be configured for cross-sectional placement within the system or device. A cross-sectional configuration of a UTI indicator substrate brings the urine into contact with the UTI indicator substrate without impairing the flow of urine through the urinary drainage system. In such a cross-sectional embodiment, a signal indicating the presence or absence of a marker indicative of a UTI can be visualized, for example, by a colorimetric change in all or a portion of the UTI indicator substrate.

A UTI indicator substrate for use in either a UTI-monitoring system or a UTI-monitoring device generally includes a detector component and a signal component. The detector component detects the presence or absence of one or more markers that are indicative of a UTI, and the signal component provides an indication, usually visual, of the presence or absence of one or more of such markers. Depending upon the particular interaction between the components, the detector component and the signal component can be together as (or on) a single moiety, or the components can be two (or more)

moieties. Two (or more) moieties may be separated (e.g., spatially), or may co-exist at essentially the same position on the indicator substrate. In some instances, two (or more) moieties may be physically attached to one another, for example, with covalent bonds. In some instances, the detector component and the signal component of a UTI indicator substrate can be placed directly on a wall of a portion of the system or of a device without the presence of an actual 'substrate.'

Detector and signal components are used routinely in the art of laboratory testing and diagnostics. For example, dipstick tests, home pregnancy tests, tests for strep throat (e.g., Rapid Strep Test®), glucose meters, and tuberculosis DFA tests all utilize some form of detector and signal components. See, for example, Vaitukaitis et al., 1972, Am. J. Obst. Gynecol., 113:751-8; and U.S. Pat. Nos. 5,602,040; 5,622,871; 5,656,503; and 5,712,172 and references cited therein. A UTI indicator substrate can be configured in a number of different ways including a reagent strip, a coated bead, or other suitable means used in the art. A UTI indicator substrate can be made of durable material(s) that can maintain the integrity of the detector and signal components following exposure to urine for an extended period of time, or the UTI indicator substrate can be periodically changed and scored immediately or shortly after exposure to urine.

As described herein, a UTI indicator substrate detects one or more markers in urine that are indicative of a UTI. Detector components are known in the art. Representative detector components include, without limitation, antibodies (for antigen-specific binding) or antigens (for antibody-specific binding). Immunoassays and enzymatic assays are routine in the art, and numerous methods are known in the art for detecting markers in body fluids such as urine. See, for example, *Current Protocols in Immunology,* 1997, Coligan et al., Eds., John Wiley & Sons, Inc., NY; *Current Protocols in Molecular Biology,* 1997, Ausubel et al., Eds., John Wiley & Sons, Inc., NY; and U.S. Pat. Nos. 3,438,737; 3,359,072; 3,418,079; and 4,013,416.

A marker found in urine that is indicative of a UTI is leukocyte esterase, also known as white blood cell (WBC) esterase. The presence of leukocyte esterase in urine is an indication that white blood cells are present, which indicates infection of one or more structures of the urinary tract. See, for example, Simerville et al., 2005, *Am. Fam. Physician,* 71:1153-62; Young et al., 2001, *Infect. Dis. Obstet. Gynecol.,* 9:249-55. Czerwinski et al., 1971, *Amer. J. Obstet. Gynec.,* 10:677; Notelovitz et al., 1970, *S. A. Med. J.,* 44:1128; and Beer et al., 1996, *Brit. Med. J.,* 313:25; and U.S. Pat. Nos. 4,278,763; 4,331,760; 4,469,789; 4,551,428; 4,637,979; 4,645,842; 4,657,855; 4,704,460; 4,758,508; 5,512,450; 5,663,044; 5,776,780; 6,013,465; and 6,855,491. In addition to or as an alternative to detecting leukocyte esterase, the level of nitrites in the urine can be used to monitor a patient for a UTI. Nitrites are typically present in a patient developing or having a UTI because many species of bacteria that colonize the urine and urinary tract convert nitrates derived from dietary metabolites into nitrites. See, for example, Fuchs & Gutensohn, 1967, *Dtsch. Med. J.,* 10:343; and U.S. Pat. Nos. 4,434,235; 5,759,860; and 5,776,715.

Representative signal components include, without limitation, a chemical reaction, a colorimetric reaction, a photochemical reaction, fluorescence, or the like. The result of the signal component (i.e., the indication of the presence or absence of one or more compounds indicative of a UTI) can be, for example, visible to the user. A signal can be in the form of a color change (e.g., red in the presence of a marker indicative of a UTI and white in the absence of the marker), a symbol (e.g., "+" or "−"), words (e.g., "yes" or "no"), or any combination thereof to signify the presence or absence of one or more markers in the urine indicative of a UTI. In yet another embodiment, a detector component can be coupled to a light or other electronic signal at the bedside, the nursing station, or remotely via wireless means.

Figure 3:
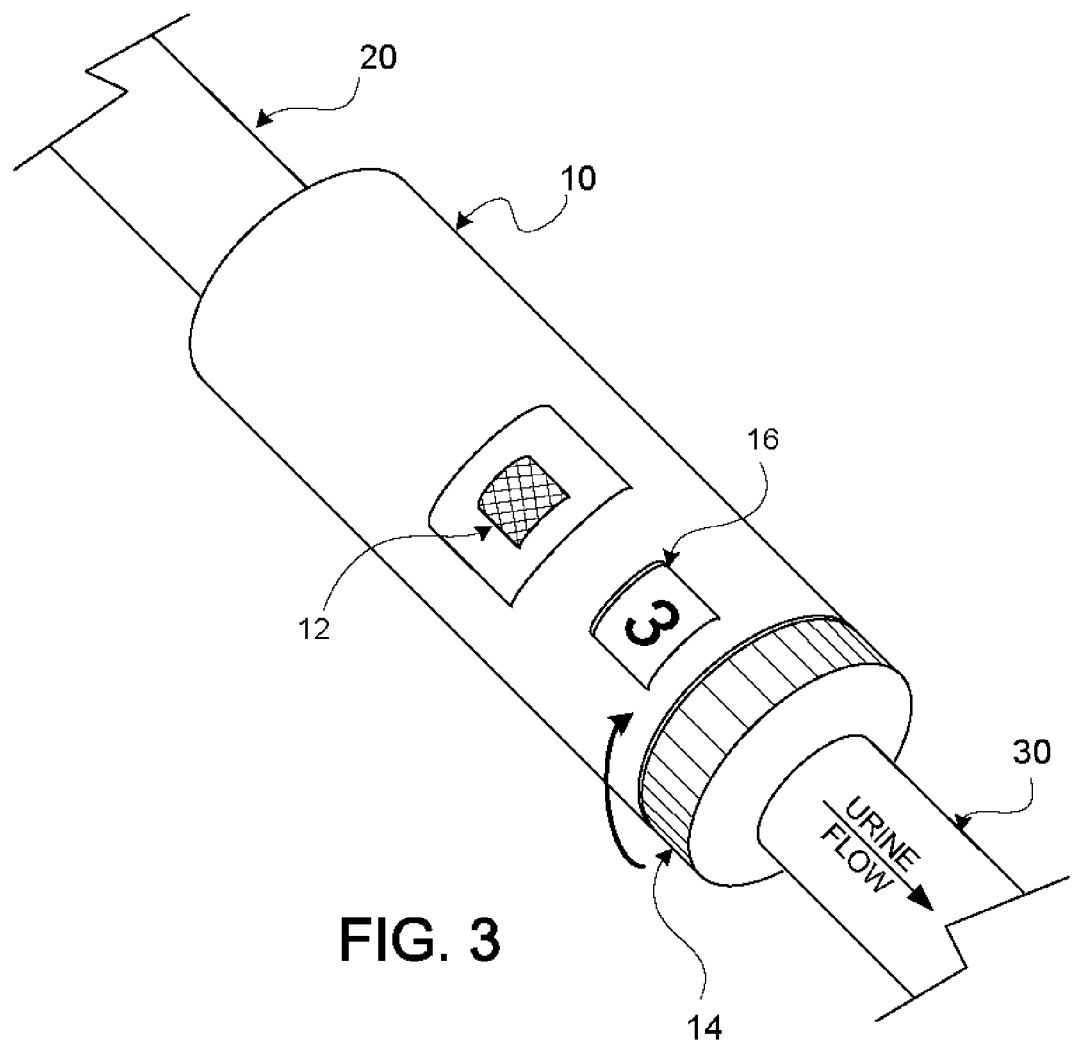
FIG. 3 is a schematic showing an embodiment of a UTI-monitoring device having multiple UTI indicator substrates contained within a dialing- or ratcheting-type mechanism.

In some embodiments, a UTI-monitoring system or device can be configured to contain multiple UTI indicator substrates. FIG. 3 shows an embodiment of a single use in-line UTI-monitoring device containing multiple UTI indicator substrates for use over a period of time. The device shown in FIG. 3 contains a rotary-type dial or a ratcheting-type knob 14 or other similar mechanism that, when employed, exposes a fresh UTI indicator substrate (e.g., a fresh detector component) to the urine flow. The dialing or ratcheting movement may break a seal, peel away a protective layer, open a blister-pack, or move, for example, a detector component from a closed or sealed portion of the device into contact with the urine. Although the dialing- or ratcheting-type embodiment shown in FIG. 3 is configured for in-line placement in a urinary catheter system, a dialing- or ratcheting-type embodiment is not limited to such a design. For example, a UTI-monitoring system or device can be designed to receive a cartridge or cassette or the like containing multiple UTI indicator substrates. A dialing- or ratcheting-type of UTI-monitoring device having multiple UTI indicator substrates or a cartridge or cassette or the like also can have a numerical indicator 16 to track usage.

In addition to monitoring the presence or absence of markers in urine that are indicative of a UTI, a UTI-monitoring urinary catheter system or a UTI-monitoring device can be configured to monitor other markers, compounds, reagents, drugs, metabolites, or other characteristics or qualities of the urine. For example, specific gravity, pH, protein, glucose, ketones, bile, hemoglobin (blood), urobilinogen, sodium, potassium, or any combination thereof can be monitored in the urine. In addition, a UTI indicator substrate as described herein can be configured to monitor, for example, a substance (e.g., a drug) to determine or maintain, for example, a threshold level (e.g., maximal therapeutic value without toxicity) using methods routine in the art.

In clinical use, a UTI indicator substrate associated with either a UTI-monitoring urinary catheter system or a UTI-monitoring device can be readily scored, for example, at each periodic check of the patient's vital signs. In an embodiment in which a UTI-monitoring device or system contains multiple UTI-indicator substrates (e.g., a dialing- or ratcheting-type embodiment), the dial or knob can be rotated to expose a new UTI indicator substrate to the urine and immediately scored by the nurse or attendant checking vital signs. When a positive signal is noted, the patient's physician can be contacted for further orders or a pre-determined protocol can be activated based on the patient's clinical scenario and medical history. FIG. 4 shows representative standing orders that might be used by a physician when a UTI-monitoring system or device as described herein is employed. For example, an appropriate antibiotic regimen can be initiated while awaiting formal laboratory results on the patient's urine.

The use of a UTI-monitoring system or device such as that disclosed herein can detect a UTI or a potential UTI very early in its course and allow for prompt treatment. The UTI-monitoring systems and devices described herein can significantly reduce the risks associated with indwelling urinary catheters and improve the standard of care for such patients. The UTI-monitoring systems and devices described herein are of particular value to patients that are at high risk of developing a UTI (e.g., patients requiring a long-term urinary catheter)

such as head injury patients, patients having a broken spinal cord or a broken pelvis, or comatose patients and may be the difference between life and death for an immunocompromised high-risk patient such as a burn patient. The UTI-monitoring systems and devices, however, can be used by any catheterized patient (e.g., a woman in labor, or a patient undergoing outpatient surgery).

The UTI-monitoring systems and devices described herein can result in a significant decrease in the morbidity and mortality of catheter-associated UTIs, which are usually very responsive to treatment once identified. Use of a UTI-monitoring system or device also can result in substantial financial savings by cost-effectively treating UTIs at an early stage, thereby preventing the progression to more life threatening and costly systemic infections.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A urinary tract infection (UTI)-monitoring urinary catheter system for monitoring the presence or absence of one or more markers in urine that are indicative of a urinary tract infection (UTI) comprising a catheter portion, a collection tubing portion, and a collection bag portion, wherein said collection tubing portion or said collection bag portion further comprises multiple UTI indicator substrates, wherein said multiple UTI indicator substrates are configured to be serially exposed to multiple freshly voided urine specimens, wherein said multiple UTI indicator substrates are sequestered from the urine but, when exposed to a freshly voided urine specimen, are capable of detecting and signaling the presence or absence of one or more markers in said freshly voided urine specimen that are indicative of a UTI.

2. The UTI-monitoring urinary catheter system of claim 1, wherein said UTI indicator substrate is separately and sequentially exposed to urine inside of said collection tubing portion or said collection bag portion.

3. The UTI-monitoring urinary catheter system of claim 1, wherein said multiple UTI indicator substrates are releasably attached to an inside surface of said collection tubing portion or said collection bag portion.

4. The UTI-monitoring urinary catheter system of claim 1, wherein each of said multiple UTI indicator substrates detects leukocyte esterase.

5. The UTI-monitoring urinary catheter system of claim 4, wherein each of said multiple UTI indicator substrates further detects nitrites.

6. The UTI-monitoring urinary catheter system of claim 1, wherein at least one of said multiple UTI indicator substrates detects nitrites.

7. The UTI-monitoring urinary catheter system of claim 1, wherein the UTI indicator substrate comprises an antibody that has a specific binding affinity for said one or more markers in urine that are indicative of a UTI.

8. The UTI-monitoring urinary catheter system of claim 1, wherein the presence of one or more markers in said freshly voided urine is indicated by a word, symbol, or colorimetric change.

9. The UTI-monitoring urinary catheter system of claim 1, wherein the signaling the presence or absence of one or more markers in said freshly voided urine specimen that are indicative of a UTI is a word, symbol, or colorimetric change.

10. The UTI-monitoring urinary catheter system of claim 1, wherein the signaling the presence or absence of one or more markers in said freshly voided urine specimen that are indicative of a UTI comprises an electronic signal.

11. The UTI-monitoring urinary catheter system of claim 10, wherein the electronic signal is a digital read out or a light.

12. The UTI-monitoring urinary catheter system of claim 10, wherein the electronic signal is at a location that is remote from said UTI-monitoring urinary catheter system.

13. An UTI monitoring device for monitoring the presence or absence of one or more markers in urine that are indicative of a urinary tract infection comprising
a first port on one end and a second port on the other end, wherein said first and second ports are configured for in-line placement within a urinary catheter system, wherein, located between said first and second ports are multiple UTI indicator substrates, wherein said multiple UTI indicator substrates are configured to be serially exposed to multiple freshly voided urine specimens, wherein said multiple UTI indicator substrates are sequestered from the urine but, when exposed to a freshly voided urine specimen, can detect and signal the presence or absence of said one or more markers in said freshly voided urine specimen that are indicative of a UTI.

14. A urinary tract infection (UTI)-monitoring urinary catheter system for monitoring the presence or absence of one or more markers in urine that are indicative of a urinary tract infection (UTI) comprising a catheter portion, a collection tubing portion, and a collection bag portion, wherein said collection tubing portion or said collection bag portion further comprises multiple UTI indicator substrates, wherein said multiple UTI indicator substrates are configured to be serially exposed to multiple freshly voided urine specimens, wherein said multiple UTI indicator substrates are sequestered from the urine but, when exposed to a freshly voided urine specimen, are capable of detecting and signaling the presence or absence of one or more markers in said freshly voided urine specimen that are indicative of a UTI, wherein said signaling comprises a visible signal.

15. The UTI-monitoring urinary catheter system of claim 14, wherein said visible signal is a word, symbol, or colorimetric change.

16. The UTI-monitoring urinary catheter system of claim 14, wherein the visible signal is an electronic signal.

17. The UTI-monitoring urinary catheter system of claim 16, wherein the electronic signal is a digital read out or a light.

18. The UTI-monitoring urinary catheter system of claim 16, wherein the electronic signal is at or near a patient using the UTI-monitoring urinary catheter system.

19. The UTI-monitoring urinary catheter system of claim 16, wherein the electronic signal is at a location remote from a patient using the UTI-monitoring urinary catheter system.

* * * * *